United States Patent [19]

Gittos et al.

[11] Patent Number: 4,529,733
[45] Date of Patent: Jul. 16, 1985

[54] ANTIHYPERTENSIVE 3-FUROYL-1,4-DIHYDROPYRIDINES

[75] Inventors: Maurice W. Gittos, Plobsheim; Michael Spedding, Wolfisheim, both of France

[73] Assignee: Merrell Dow Pharmaceuticals Inc., Cincinnati, Ohio

[21] Appl. No.: 592,184

[22] Filed: Mar. 22, 1984

[30] Foreign Application Priority Data

Apr. 6, 1983 [GB] United Kingdom ............... 8309284

[51] Int. Cl.³ ............... C07D 405/06; A61K 31/455
[52] U.S. Cl. ............................ 514/336; 546/283; 514/929
[58] Field of Search ................. 546/283; 424/266

[56] References Cited

U.S. PATENT DOCUMENTS 3,775,422 11/1973 Bossert et al. ............... 546/321

Primary Examiner—Henry R. Jiles
Assistant Examiner—Dale A. Bjorkman
Attorney, Agent, or Firm—William J. Stein; Raymond A. McDonald; Gary D. Street

[57] ABSTRACT

Novel 1,4-dihydropyridine derivatives have the following general Formula:

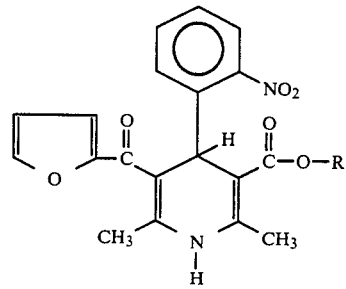

and are calcium antagonists, useful for treating cardiovascular diseases.

7 Claims, No Drawings

ANTIHYPERTENSIVE 3-FUROYL-1,4-DIHYDROPYRIDINES

The drugs characterized as calcium antagonists are known to produce various therapeutically useful pharmacological effects, especially cardiovascular effects. Such drugs have been used clinically in the treatment of diverse cardiac diseases or conditions, such as arterial hypertension, angina pectoris, and arrhythmias, and in certain circumstances left ventricular failure, acute myocardial infarction, cardiac preservation, cardiomyopathy, cerebral vasospasm, and other vasospastic syndromes [See P. Henry, The American Journal of Cardiology 46, 1047 (1980)]. Examples of calcium antagonists are: nifedipine, nimodipine, nicardipine, diltiazem, papaverine, prenylamine, verapamil, fendiline, cinnarizine, flunarizine, and PY108068 (Sandoz).

An important class of calcium antagonists are the 4-aryldihydropyridines of which nifedipine, 4-(2'-nitrophenyl)-2,6-dimethyl-3,5-dicarbomethoxy-1,4-dihydropyridine, is marketed in the U.K. and certain other countries as Adalat (TM, Bayer). Nifedipine is described on pages 1628–1629, "Martindale, The Extra Pharmacopoeia", J. Reynolds, Ed., Council of the Pharmaceutical Society of Great Britain, The Pharmaceutical Press, London, 1982, and in U.S. Pat. Nos. 3,485,847 and 3,644,627. The scientific literature pertaining to the pharmacological and physiological effects of nifedipine is extensive [See, for example, P. Henry, supra; H. Mueller et al., *Pharmacotherapy*, Vol. 1, No. 2, Sept/Oct, 1981; M. Spedding, *Journal of Cardiovascular Pharmacology*, 4, 973 (1982); M. Spedding, *Naunyn-Schmiedeberg's Arch. Pharmacology*, 318, 234 (1982); and *Calcium Blockers*, Flaim and Zelis, Eds., Urban and Schwarzenburg, Publishers, Baltimore, 1982].

The present invention relates to novel 1,4-dihydropyridine derivatives of general Formula I:

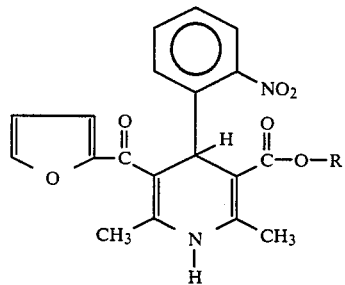

wherein R is methyl, ethyl, n-propyl, isopropyl, or methoxyethyl.

The preferred compounds of general Formula I contemplated by the present invention are:
3-(2-furoyl)-5-methoxycarbonyl-2,6-dimethyl-4-(2-nitrophenyl)-1,4-dihydropyridine, and
3-(2-furoyl)-5-ethoxycarbonyl-2,6-dimethyl-4-(2-nitrophenyl)-1,4-dihydropyridine.

The compounds of general Formula I are calcium antagonists and are useful for treating certain cardiovascular diseases or conditions. In general, the compounds of general Formula I can be used therapeutically for the treatment of those cardiovascular diseases or conditions that are susceptible to treatment by nifedipine, and they can be employed in treating such diseases or conditions in a manner analogous to nifedipine. Preferably, the compounds of general Formula I can be used for treating angina pectoris and arterial hypertension.

The use of the compounds of general Formula I in the treatment of cardiovascular diseases or conditions offer a significant and unexpected advantage over the use of nifedipine, and other related 4-aryldihydropyridines, in that the compounds of general Formula I will produce greater direct bradycardia resulting in a decrease in reflex tachycardia at equipotent therapeutic doses.

The calcium antagonist properties of the compounds of general Formula I can be demonstrated in vitro in standard pharmacological test procedures. For example, calcium antagonism can be demonstrated in $K^+$-depolarized taenia preparations from the guinea pig caecum using the method of M. Spedding, *Naunyn-Schmiedeberg's Arch. Pharmacol.*, 38, 234 (1982). In this test, 3-(2-furoyl)-5-methoxycarbonyl-2,6-dimethyl-4-(2-nitrophenyl)-1,4-dihydropyridine and 3-(2-furoyl)-5-ethoxycarbonyl-2,6-dimethyl-4-(2-nitrophenyl)-1,4-dihydropyridine caused a concentration-dependent displacement to the right of concentration-response curves to $Ca^{++}$. The calculated $pA_2$ values for 3-(2-furoyl)-5-methoxycarbonyl-2,6-dimethyl-4-(2-nitrophenyl)-1,4-dihydropyridine and 3-(2-furoyl)-5-ethoxycarbonyl-2,6-dimethyl-4-(2-nitrophenyl)-1,4-dihydropyridine are $8.75 \pm 0.10$ and $8.34 \pm 0.09$, respectively. The published $pA_2$ value for nifedipine is $9.8 \pm 0.1$ [See M. Spedding, *Naunyn-Schmiedeberg's Arch. Pharmacol.*, 318, 234 (1982)].

Calcium antagonism can also be demonstrated by the inhibition of $^{45}Ca^{++}$ uptake in $K^+$-depolarized taenia preparations from guinea pig caecum. In this procedure, strips of taenia are incubated in $Ca^{++}$-free buffer (composition, mM: NaCl, 97; KCl, 40; glucose, 5.5, HEPES buffer, 10; pH 7.0) at 35° C. and gassed with oxygen. The preparations thus prepared are then incubated with the test compound for 20 minutes after which $^{45}Ca^{++}$/$Ca^{++}$ is added (1 mM for 10 minutes). Extracellular $Ca^{++}$ is displaced with lanthanum (50 mM) at 0°–4° C. When tested according to the above procedure, 3-(2-furoyl)-5-methoxycarbonyl-2,6-dimethyl-4-(2-nitrophenyl)-1,4-dihydropyridine at 0.1 and 1 μM reduced uptake of $^{45}Ca^{++}$ into the tissue.

The anti-hypertensive effects of the compounds of general Formula I can be demonstrated using standard in vivo pharmacological test procedures in laboratory animals. For example, the anti-hypertensive activity of the compounds of general Formula I can be demonstrated in pithed rats using the method of M. Spedding, *J. Cardiovascular Pharmacol.*, 4, 973 (1982). In this test, active compounds reduce blood pressure elevated by an infusion of angiotensin II. The heart rate of the animals is also determined. The results of the testing of 3-(2-furoyl)-5-methoxycarbonyl-2,6-dimethyl-4-(2-nitrophenyl)-1,4-dihydropyridine (Compound A), 3-(2-furoyl)-5-ethoxycarbonyl-2,6-dimethyl-4-(2-nitrophenyl)-1,4-dihydropyridine (Compound B), and nifedipine are shown below:

| Dose i.v. (nmol/kg) | Change (% control) | |
|---|---|---|
| | Diastolic blood pressure | Heart rate |
| Compound A (n = 8): | | |
| 3 | 82.2 ± 5.3 | 98.1 ± 0.9 |
| 10 | 72.3 ± 4.9 | 93.7 ± 1.7 |
| 30 | 62.4 ± 3.5 | 90.9 ± 2.5 |
| 100 | 52.0 ± 3.8 | 81.1 ± 3.3 |
| 300 | 45.0 ± 1.6 | 74.2 ± 3.4 |
| 1000 | 36.4 ± 1.8 | 67.9 ± 3.4 |

| Dose i.v. | Change (% control) | |
|---|---|---|
| (nmol/kg) | Diastolic blood pressure | Heart rate |
| 3000 | 32.9 ± 1.8 | 64.3 ± 3.4 |
| Compound B (n = 6): | | |
| 3 | — | — |
| 10 | 80.6 ± 2.8 | 94.1 ± 0.5 |
| 30 | 67.9 ± 3.0 | 90.4 ± 1.3 |
| 100 | 47.7 ± 2.4 | 85.7 ± 1.5 |
| 300 | 45.6 ± 3.9 | 84.1 ± 3.4 |
| 1000 | 39.1 ± 2.1 | 76.6 ± 3.4 |
| 3000 | 37.1 ± 0.8 | 72.2 ± 3.4 |
| Nifedipine (n = 3-5): | | |
| 3 | — | — |
| 10 | 92.5 ± 3.5 | 100 |
| 30 | 74.6 ± 7.9 | 97.6 ± 1.3 |
| 100 | 56.3 ± 4.6 | 98.2 ± 1.8 |
| 300 | 50.1 ± 1.3 | 92.2 ± 2.7 |
| 1000 | 19.5 ± 5.9 | 91.9 ± 2.9 |
| 3000 | — | — |

The results given above indicate that 3-(2-furoyl)-5-methoxycarbonyl-2,6-dimethyl-4-(2-nitrophenyl)-1,4-dihydropyridine, 3-(2-furoyl)-5-ethoxycarbonyl-2,6-dimethyl-4-(2-nitrophenyl)-1,4-dihydropyridine, and nifedipine significantly reduced diastolic blood pressure, elevated by an infusion of angiotensin II, in a dose-dependent manner. In addition, 3-(2-furoyl)-5-methoxycarbonyl-2,6-dimethyl-4-(2-nitrophenyl)-1,4-dihydropyridine and 3-(2-furoyl)-5-ethoxycarbonyl-2,6-dimethyl-4-(2-nitrophenyl)-1,4-dihydropyridine produced a dose-dependent bradycardia, which is not prominent with nifedipine. The difference between 3-(2-furoyl)-5-methoxycarbonyl-2,6-dimethyl-4-(2-nitrophenyl)-1,4-dihydropyridine and nifedipine may reflect different tissue selectivities which can be made clinically manifest in several ways, as for example, via reduced tachycardia or via increased effects in other tissues leading to vasodilation or diuresis.

The anti-hypertensive effects of the compounds of general Formula I can also be demonstrated in pentobarbitone-anesthetized rats. In this test, rats, anesthetized with a 45 to 60 mg/kg dose (i.p.) of sodium pentabarbitone, receive the test compound by injection by means of an indwelling cannula in the femoral vein. Diastolic blood pressure is measured by an indwelling catheter in the femoral artery. Heart rate is also measured. The results of the testing of 3-(2-furoyl)-5-methoxy-carbonyl-2,6-dimethyl-4-(2-nitrophenyl)-1,4-dihydro-pyridine (Compound A) and nifedipine are given below:

| Dose (i.v.) | Change (% control) | |
|---|---|---|
| (nmol/kg) | Diastolic blood pressure | Heart rate |
| Compound A (n = 7): | | |
| 10 | 86.0 ± 3.3 | 103.5 ± 0.9 |
| 30 | 80.2 ± 3.2 | 106.2 ± 2.0 |
| 100 | 55.0 ± 2.8 | 107.1 ± 3.6 |
| 300 | 54.6 ± 1.9 | 106.7 ± 3.1 |
| 1000 | 46.7 ± 1.6 | 104.0 ± 1.8 |
| 3000 | 46.6 ± 1.6 | 102.2 ± 2.2 |
| 10000 | 32.4 ± 2.0 | 99.9 ± 3.4 |
| Nifedipine (n = 7): | | |
| 10 | 87.0 ± 3.7 | 108.3 ± 2.0 |
| 30 | 86.6 ± 3.6 | 113.5 ± 2.2 |
| 100 | 62.9 ± 3.6 | 121.1 ± 3.3 |
| 300 | 68.3 ± 4.3 | 118.1 ± 4.0 |
| 1000 | 54.2 ± 4.7 | 117.3 ± 5.2 |
| 3000 | 37.2 ± 3.1 | 113.0 ± 3.9 |
| 10000 | — | — |

The above results indicate that 3-(2-furoyl)-5-methoxycarbonyl-2,6-dimethyl-4-(2-nitrophenyl)-1,4-dihydropyridine and nifedipine reduced blood pressure in anesthetized rats in a dose-dependent manner. However, a comparison of the changes in heart rate shows that nifedipine produced significantly more reflex tachycardia than 3-(2-furoyl)-5-methoxycarbonyl-2,6-dimethyl-4-(2-nitrophenyl)-1,4-dihydropyridine.

The anti-hypertensive effect of the compounds of general Formula I can also be demonstrated in conscious spontaneously hypertensive rats (stroke prone strain). In this test, the test compound is injected in an indwelling cannula in the femoral vein and blood pressure is measured by an indwelling catheter in the femoral artery. Heart rate is also measured. The results of the testing of 3-(2-furoyl)-5-methoxycarbonyl-2,6-dimethyl-4-(2-nitrophenyl)-1,4-dihydropyridine (Compound A) and nifedipine are shown below:

| Dose (i.v.) (nmol/kg) | Fall in mean blood pressure (mm Hg) | Increase in heart rate (beats/min) |
|---|---|---|
| Compound A (n = 5): | | |
| 100 | 4.5 ± 1.5 | 20.0 ± 3.2 |
| 300 | 20.5 ± 1.5 | 70.0 ± 4.2 |
| 1000 | 42.5 ± 1.8 | 118.0 ± 16.3 |
| 3000 | 56.6 ± 1.4 | 136.3 ± 11.1 |
| Nifedipine (n = 5): | | |
| 100 | 7.0 ± 1.5 | 24.0 ± 2.5 |
| 300 | 22.5 ± 3.5 | 57.0 ± 5.8 |
| 1000 | 43.1 ± 3.4 | 112.5 ± 4.8 |
| 3000 | 63.1 ± 5.6 | 125.0 ± 13.2 |

The above results indicate that 3-(2-furoyl)-5-methoxycarbonyl-2,6-dimethyl-4-(2-nitrophenyl)-1,4-dihydropyridine and nifedipine significantly reduced blood pressure in a dose-dependent manner. However, a comparison of the changes in heart rate shows that both compounds produced reflex tachycardia. This result may not necessarily relate to other species, such as man, since it is known that in spontaneously hypertensive rats the sympathetic nervous system is hyperactive [J. Fozard et al., Journal of Cardiovascular Pharmacology, 3, 1038 (1981)].

For the treatment of the aforesaid cardiovascular diseases or conditions, the dosage of the compounds of general Formula I in warm blooded animals will depend upon the species being treated, the particular compound employed, the nature and severity of the disease or condition being treated, and the mode of administration. In general, an effective dosage capable of providing a physiologically useful cardiovascular effect can be achieved in warm blooded animals at a dose of from about 0.1 mg/kg to about 40 mg/kg (body weight) per day administered orally or parenterally. For large animals (about 70 kg), a dosage of about 0.1 mg/kg to about 20 mg/kg (preferably 0.2 mg/kg to 10 mg/kg) per day can be employed. Therapy should be initiated at a lower dose, the dosage thereafter being increased in small intervals until the desired effect is achieved.

The compounds of general Formula I can be administered in various manners to achieve the desired effect. The compounds can be administered alone or in combination with pharmaceutically acceptable carriers or diluents, the proportion and nature of which are determined by the solubility and chemical properties of the compound selected, the chosen route of administration, and standard pharmaceutical practice. Preferably, the compounds of Formula I may be administered orally or sublingually in solid dosage forms, e.g. capsules or tablets, which may contain conventional excipients. Slow-release dosage forms may also be employed.

The amount of active compound administered will vary and can be any effective amount. Unit doses of these compounds can contain, for example, from about 1 mg to 100 mg of the compounds and may be administered, for example, one or more times daily, as needed.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms, such as scored tablets, said predetermined unit will be one fraction such as a half or quarter of a scored tablet, of the multiple dose form.

In the composition aspect of the invention, there are provided phrmaceutical formulations in which form the active compounds of the invention will normally be utilized. Such formulations are prepared in a manner well known per se in the pharmaceutical art and usually comprise at least one active compound of the invention in admixture or otherwise in association with a pharmaceutically acceptable carrier or diluent therefor. A carrier or diluent may be solid, semi-solid, or liquid material which serves as a vehicle, excipient, or medium for the active ingredient. Suitable diluents or carriers are well known per se. Preferred pharmaceutical formulations are those adapted for oral or sublingual use which may be administered to the patient in the form of tablets or capsules, or the like.

The compounds of general Formula I can be prepared in a manner known per se by reacting 2-(2-furoyl)-1-(2-nitrophenyl)-3-oxobut-1-ene with a compound of general Formula II:

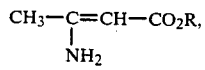

wherein R is ethyl, methyl, n-propyl, isopropyl, or methoxyethyl, in an inert organic solvent at a temperature ranging from about 60° C. to about 120° C. and a reaction time ranging from about 4 to about 48 hours. A preferred solvent is a lower alkanol, such as ethanol. The preferred reaction temperature is about 80° C. When ethanol is employed, it is convenient to carry out the reaction at reflux temperature and a reaction time of about 16 hours.

Since the compounds of general Formula I are light-sensitive, all preparative operations should be performed in such a manner so as to protect the compounds from light. The compounds of general Formula I should also be protected from light during storage and handling.

The preparation of 2-(2-furoyl)-1-(2-nitrophenyl)-3-oxobut-1-ene is illustrated herein in Examples 1 and 2.

The compounds of general Formula II are either known compounds or can be made in known manner from known compounds.

It will be recognized by those skilled in the art that the compounds of general Formula I contain a chiral center and that, therefore, the compounds of general Formula I can be in the form of an individual enantiomer or a mixture of the enantiomers, such as the racemate. It will be understood that, unless otherwise indicated, the compounds of the invention depicted by general Formula I or described by chemical names are in the form of the biologically active individual enantiomer or a mixture of the enantiomers, in particular the racemate. The individual enantiomers of the compounds of general Formula I can be obtained in manner known per se, such as by resolution of the corresponding free acids with a chiral base, for example brucine or strychnine.

The following non-limiting Examples further illustrate the invention.

EXAMPLE 1

1-(2-Furyl)-1,3-dioxobutane

A mixture of methyl 2-furoate (23 g, 0.18 mole) and acetone (10.6 g, 0.18 mole) was slowly added to a stirred suspension of potassium tert-butoxide (41 g, 0.36 mole) in anhydrous toluene (300 ml) at 0° C. Upon standing overnight at room temperature, glacial acetic acid (22 ml, 0.36 mole) and then water (100 ml) were added. The organic layer was separated, combined with an ether extract of the aqueous phase, washed with water, dried, and distilled to give 1-(2-furyl)-1,3-dioxobutane: b.p. 66°−70° C./0.1 mm (18.5 g).

EXAMPLE 2

2-(2-Furoyl)-1-(2-nitrophenyl)-3-oxobut-1-ene

A mixture of 1-(2-furyl)-1,3-dioxobutane (7.6 g, 0.05 mole), obtained as in Example 1, 2-nitrobenzaldehyde (7.5 g, 0.05 mole), piperidine acetate (0.2 g), and benzene (150 ml) was refluxed in a Dean and Stark apparatus for a period of 2 hours. The solution was evaporated and the residue purified using a silica column and an eluant consisting of a mixture ethyl acetate-hexane (30:70). The purified material was recrystallized from a mixture ethyl acetate and hexane to give 2-(2-furoyl)-1-(2-nitrophenyl)-3-oxobut-1-ene (7 g).

EXAMPLE 3

3-(2-Furoyl)-5-methoxycarbonyl-2,6-dimethyl-4-(2-nitrophenyl)-1,4-dihydropyridine All operations described below were carried out in the dark or in an apparatus protected from light.

A mixture of 2-(2-furoyl)-1-(2-nitrophenyl)-3-oxobut-1-ene (6.53 g, 0.023 mole), obtained as in Example 2, methyl 3-aminocrotonate (2.66 g, 0.0023 mole), and ethanol (100 ml) was refluxed in a Soxhlet apparatus containing molecular sieves (type 3A) overnight and the solvent evaporated. Crystallization of the residue from a mixture of ethyl acetate and hexane gave crystals of the required dihydropyridine derivative containing ethyl acetate of crystallization. These were dried at 110° C. to give an amorphous residue of pure 3-(2-furoyl)-5-methoxycarbonyl-2,6-dimethyl-4-(2-nitrophenyl)-1,4-dihydropyridine (5.6 g): m.p. 90°–92° C.

H'NMR 60 MHZ (CDCl$_3$): δ 1.92 (3H, s); 2.3 (3H, s); 3.5 (3H, s); 5.7 (1H, s); 6.32 (1H, m); 6.55 (1H, m); and 7.0–7.6 (6H, m).

Analysis for $C_{20}H_{18}N_2O_6$: Found: C, 62.47; H, 4.83; N, 7.17% Required: C, 62.83; H, 4.75; N, 7.32%

EXAMPLE 4

3-(2-Furoyl)-5-ethoxycarbonyl-2,6-dimethyl-4-(2-nitrophenyl)-1,4-dihydropyridine The title compound is prepared using the procedure of Example 3 starting from ethyl 3-aminocrotonate in place of methyl 3-aminocrotonate: m.p. 133°–134° C.

H'NMR 60 MHZ (CDCl$_3$): δ 1.08 (3H, s); 1.9 (3H, s); 2.38 (3H, s); 4.0 (2H, g); 5.8 (1H, s); 5.95 (1H, m); 6.5 (1H, m); and 7.0–7.7 (6H, m).

Analysis for $C_{21}H_{20}N_2O_6$: Found: C, 63.52; H, 5.15; N, 6.92% Required: C, 63.64; H, 5.09; N, 7.07%

We claim:

1. A 3-(2-furoyl)-5-alkoxycarbonyl-2,6-dimethyl-4-(2-nitrophenyl)-1,4-dihydropyridine having the formula:

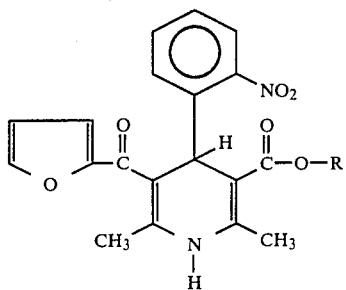

wherein R is methyl, ethyl, n-propyl, isopropyl or methoxypropyl.

2. The compound 3-(2-furoyl)-5-methoxycarbonyl-2,6-dimethyl-4-(2-nitrophenyl)-1,4-dihydropyridine.

3. The compound 3-(2-furoyl)-5-ethoxycarbonyl-2,6-dimethyl-4-(2-nitrophenyl)-1,4-dihydropyridine.

4. An antihypertensive composition comprising an amount of a compound of claim 1 effective in the treatment of hypertension in admixture or otherwise associated with a pharmaceutically acceptable diluent or carrier.

5. A pharmaceutical composition according to claim 4 in dosage unit form which contains from 1 to 100 mg of a compound of claim 1 per unit dose.

6. A method of reducing blood pressure in patients in need thereof which comprises administering a therapeutically effective amount of a 3-(2-furoyl)-5-alkoxycarbonyl-2,6-dimethyl-4-(2-nitrophenyl)-1,4-dihydropyridine having the formula

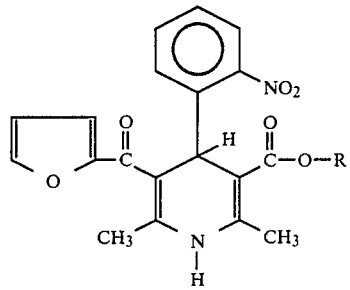

wherein R is methyl, ethyl, n-propyl, isopropyl or methoxypropyl.

7. A method according to claim 6 wherein the therapeutically effective amount is from 0.1 mg/kg to 40 mg/kg of body weight per day.

* * * * *